(12) United States Patent  
Jarman-Smith et al.

(10) Patent No.: US 8,729,150 B2  
(45) Date of Patent: May 20, 2014

(54) POLYMERIC MATERIALS

(75) Inventors: Marcus Jarman-Smith, Lancashire (GB); Andrew Holden, Lancashire (GB); Andrew Elleray, Lancashire (GB)

(73) Assignee: Invibio Limited, Lancashire (GB)

( * ) Notice: Subject to any disclaimer, the term of this patent is extended or adjusted under 35 U.S.C. 154(b) by 132 days.

(21) Appl. No.: 13/124,300

(22) PCT Filed: Oct. 14, 2009

(86) PCT No.: PCT/GB2009/051371  
§ 371 (c)(1), (2), (4) Date: May 16, 2011

(87) PCT Pub. No.: WO2010/043900  
PCT Pub. Date: Apr. 22, 2010

(65) Prior Publication Data  
US 2011/0230590 A1    Sep. 22, 2011

(30) Foreign Application Priority Data  
Oct. 17, 2008 (GB) .................................. 0819055.5

(51) Int. Cl.  
*A61F 2/28* (2006.01)

(52) U.S. Cl.  
USPC ........... 523/113; 523/114; 523/115; 424/423; 424/724; 424/722

(58) Field of Classification Search  
USPC .................. 523/113–115; 424/423, 722, 724  
See application file for complete search history.

(56) References Cited

U.S. PATENT DOCUMENTS 5,681,872 A * 10/1997 Erbe .............................. 523/114  
5,969,020 A    10/1999 Shalaby et al.

FOREIGN PATENT DOCUMENTS

| EP | 0365236 A1 | 4/1990 |
| WO | 9636368 A2 | 11/1996 |
| WO | 2007051307 A2 | 5/2007 |
| WO | 2008039488 A2 | 4/2008 |
| WO | WO 2008039488 A2 * | 4/2008 .............. A61L 27/54 |

OTHER PUBLICATIONS

Pattanayak et al., "Evaluation of Epoxy / Sodium Bioglass Ceramic Composites in Simulated Body Fluid", Trends Biomater. Artif. Organs, vol. 18 (2), Jan. 2005, pp. 225-229.

* cited by examiner

*Primary Examiner* — James J Seidleck  
*Assistant Examiner* — Peter A Salamon  
(74) *Attorney, Agent, or Firm* — Stephen F. Swinton, Jr.; Hoffman Warnick LLC

(57) ABSTRACT

Granules or pellets comprising polymeric materials such as polyaryletherketones and ceramic materials may be prepared and used to make a variety of different parts of components for use in medical applications, by melt-processing. The ceramic material may be a bioactive glass and/or a controlled-release glass, and may include less than 20 mole % sodium oxide and/or be water soluble.

20 Claims, 1 Drawing Sheet

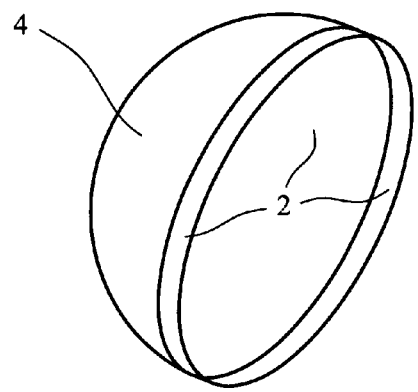
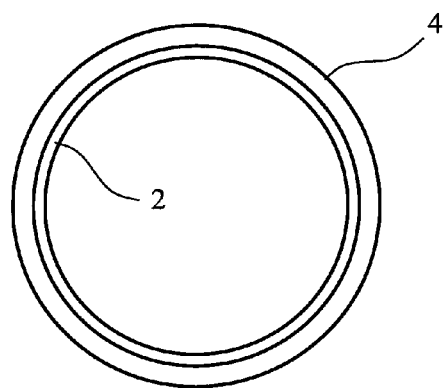
FIG. 1a                  FIG. 1b
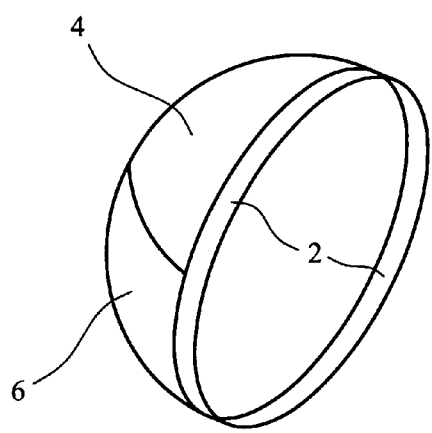
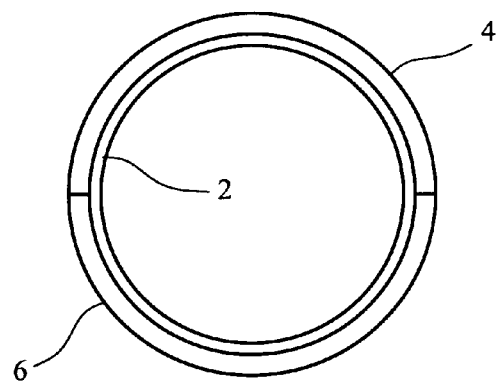
FIG. 2a                  FIG. 2b
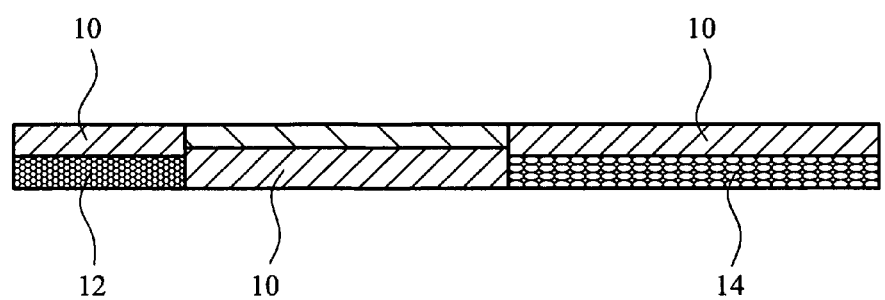
FIG. 3

POLYMERIC MATERIALS

This invention relates to polymeric material and particularly, although not exclusively, relates to porous polymeric materials for use, for example, in making medical implants or parts thereof.

It is well known to make porous medical implants and there are numerous prior art proposals. For example, WO2007/051307 discloses porous medical implants made from polyetheretherketone and salt (e.g. sodium chloride) in a process wherein the ingredients are placed in a mould cavity, compressed and heated to melt the polyetheretherketone but not the salt and form a moulded part. After subsequent cooling to solidify the mixture, the moulded material is placed in a water bath at 100° C. to dissolve the salt from the moulded part and define a porous moulded part.

U.S. Pat. No. 5,969,020 discloses microporous polymeric foams and microtextured surfaces suitable for medical applications. In preparing the foams, an organic crystalline polymer is melted and combined with a selected solid crystalline fugitive compound to produce a substantially isotropic solution. The solution is cooled under controlled conditions, which foster solid-solid phase separation by the simultaneous crystallization of the fugitive compound and the polymer, to produce a foam precursor containing the solidified fugitive compound dispersed through a matrix of the organic polymer. Crystals of fugitive compound are then removed by solvent extraction and/or sublimation, or like process to produce microcellular foams having a continuous, open-cell structure.

In such porous materials, the fugitive material must be completely removed in an appropriate process to ensure the porous material is not contaminated with any potentially toxic agents prior to implantation. Complete removal can be difficult and, accordingly, there is a risk that levels of fugitive material may remain even after (attempted) removal.

It is also known to produce medical implants made from resorbable materials containing active materials which leach from the implant and have a beneficial effect when in vivo.

In addition, it is known from Trends Biomater. Artif. Organs, Vol 18(2), 225 to combine epoxy and bioactive glasses by curing under pressure. The bioactivity of samples prepared was studied. In addition, the paper refers to attempts being made to develop composites containing polymer or metal with various bioceramics that give better mechanical properties as well as better bioactivity and suggests that "HDPE, PMMA, Epoxy, PEEK, Starch, polysulphone, polylactides are found to be useful polymers in biomedical research and composites are also fabricated using these polymers with bioglasses as well as glass ceramics."

Although prior art suggests polyetheretherketone and bioactive glasses can be combined, applicant is not aware of any disclosure wherein polyetheretherketone and a bioactive glasses have been successfully melt-processed and, in fact, the most widely available and used bioactive glasses, referred to as 45S5, cannot be melt processed with polyetheretherketone—the bioactive glass appears to react with the polymer and the polymer solidifies even at the melt processing temperature.

In fact WO2008/039488 acknowledges the difficulties in combining bioactive glasses, such as combeite glass-ceramic, with PEEK, it being stated that combination using a twin-screw extruder results in a reaction between PEEK and the glass-ceramic forming a material which inhibits extruder functioning. As a consequence, although WO2008/039488 describes composites comprising PEEK and bioactive glass, such composites are prepared in a method which involves blending the PEEK and glass in a polar organic solvent, such as an alcohol, followed by subsequent removal of the solvent to yield a homogenous blend of particles.

It is an object of embodiments of the present invention to address problems associated with the use of glasses, for example bioactive glasses, in certain polymeric materials.

It is also an object of embodiments of the present invention to utilise glasses, for example bioactive glasses, in pore formation in composite materials.

According to a first aspect of the invention, there is provided a mass of material comprising a polymeric material and a ceramic material, wherein said polymeric material is of a type which includes:
(a) phenyl moieties;
(b) ketone moieties; and
(c) ether moieties;
wherein the ceramic material is a bioactive glass and/or a controlled release glass, wherein said ceramic material includes less than 20 mole % sodium oxide and/or is water soluble.

A said bioactive glass may include less than 20 mole % sodium oxide as described; a said controlled release glass is suitably water soluble. A said bioactive glass comprising less than 20 mole % sodium oxide may be water soluble.

Said ceramic material suitably includes a glass former and a glass modifier.

A glass former may be selected from silicon dioxide, phosphorous pentoxide or boron trioxide. Said glass former preferably comprises silicon dioxide or phosphorous pentoxide.

Said ceramic material suitably includes 85 mole % or less, preferably 75 mole % or less of a said glass former.

A glass modifier may be an oxide or carbonate, for example a metal oxide or carbonate or a lanthanide oxide or carbonate. A metal of said oxide or carbonate may be an alkali or alkaline earth metal. Said ceramic material preferably includes a glass modifier selected from $Li_2O$, $Na_2O$, $K_2O$, MgO, ZnO and CaO.

The sum of the amount of glass formers and glass modifiers in said ceramic material may be at least 80 mole %, preferably at least 90 mole %, more preferably at least 95 mole %.

Said ceramic material may include other compounds in addition to said glass former and glass modifier. Less than 20 mole %, preferably less than 10 mole %, more preferably less than 5 mole % of other compounds may be included.

A bioactive glass as described is suitably able to elicit a reaction when implanted in a human body. For example, being "bioactive" may imply chemical formation of a calcium phosphate layer (amorphous, partially crystalline or crystalline) via ion exchange between surrounding fluid in vitro and the ceramic material. In vitro assessment of whether a said ceramic material is bioactive may be undertaken as described by Kokubo at Biomaterials (2006) 27:2907-2915

Said ceramic material, for example bioactive glass, may include less than 15 mole % sodium oxide, suitably less than 13 mole % sodium oxide, preferably less than 10 mole % sodium oxide, more preferably less than 7 mole % sodium oxide, especially less than 3 mole % sodium oxide. In some cases, said ceramic material may include less than 1 mole % sodium oxide, preferably 0 mole % of sodium oxide.

The total amount of alkali metal oxide in said ceramic material, for example bioactive glass, may be less than 15 mole %, suitably less than 13 mole %, preferably less than 10 mole %, more preferably less than 7 mole %, especially less than 3 mole %. In some cases, the total amount may be less than 1 mole % and is preferably 0 mole %.

A bioactive glass as described may include silicon dioxide as a glass former. It may include at least 10 mole %, suitably at least 20 mole %, preferably at least 30 mole %, more preferably at least 40 mole % of silicon dioxide. The amount of silicon dioxide may be less than 70 mole %, suitably less than 60 mole %.

A said bioactive glass which includes a high level of silicon dioxide may be insoluble in water or have low solubility.

Properties of bio-active glasses may be dependent on the network connectivity, see Journal of Materials Science Material in Medicine 10 (1999) 697-701 (Wallace) and Journal of Materials Science Letters 15 (1996) 1122-1125 (Hill). Said bio-active glass may have a network connectivity of 2 or greater, preferably greater than 2.1. The network connectivity may be less than 3.2, preferably less than 2.5. The cross-link density as discussed in the aforementioned Hill paper may be greater than −0.10, preferably greater than 0. The cross-link density may be less than 0.8.

Controlled release glasses could also be bioactive but need not be. Controlled release glasses are preferably biocompatible and/or biologically inert.

A said controlled release glass suitably includes less than 20 mole %, preferably less than 10 mole %, more preferably less than 5 mole %, especially less than 1 mole % of silicon dioxide.

A said controlled release glass may include phosphorous pentoxide as a glass former. It may include at least 10 mole %, preferably at least 20 mole %, more preferably at least 25 mole %, especially at least 30 mole % of phosphorous pentoxide. The amount of phosphorous pentoxide may be less than 85 mole % or less than 60 mole %.

A said controlled release glass suitably includes less than 15 mole %, suitably less than 13 mole %, preferably less than 10 mole %, more preferably less than 7 mole %, especially less than 5 mole % of sodium oxide.

The total amount of alkali metal oxide in said controlled release glass is suitably less than 15 mole %, suitably less than 13 mole %, preferably less than 10 mole %, more preferably less than 7 mole %, especially less than 5 mole % of alkali metal oxide.

Said controlled release glass may include an alkaline earth metal oxide or carbonate or oxide or carbonate of a lanthanide. The total amount of such oxides or carbonates in said glass may be less than 80 mole %, preferably less than 75 mole %, more preferably less than 70 mole %, especially less than 60 mole %. The total amount of such oxides or carbonates in said glass may be at least 5 mole %, preferably at least 15 mole %, more preferably at least 25 mole %. The total amount of such oxides or carbonates in said glass may be up to 40 mole %.

Said controlled release glass is preferably completely soluble in water at 38° C.

On dissolution (in isolation, i.e. not when as part of said mass of material), said controlled release glass suitably has a pH of less than 7, suitably less than 6.8, preferably less than 6.5, more preferably less than 6.

Said mass of material of the first aspect may comprise a simple mixture of said polymeric material and said ceramic material, for example wherein the two materials are not fixed to one another such as in a fused arrangement; or said mass of material may comprise a fused arrangement produced for example by melt processing the two materials together. Such melt processing may be by compression moulding, injection moulding, extrusion or the like.

In a preferred embodiment, said mass of material comprises particles which include said polymeric material and said ceramic material.

The mass of material can be used in subsequent process steps to manufacture parts, for example medical implants or parts thereof or parts having non-medical applications. The parts may be arranged to be bioactive and/or encourage formation of bone or other tissues in, on or around a medical implant or part incorporating the mass of material. In some embodiments, the ceramic material may be arranged to act as a fugitive material. In this case, the ceramic material may be removed in a dissolution process (using a non-aqueous or, preferably, an aqueous solvent) either before use of the part or subsequently. A part wherein the ceramic material acts as a fugitive material may be used in medical or non-medical applications. When the ceramic material is arranged to be removed during use of the part, dissolution of the ceramic material may be arranged to release an active material which had been incorporated in the part. In this case, the part may have a functional effect and/or act as a delivery vehicle for the active material. In medical applications, the ceramic material may be arranged to be removed in vivo, (or it may be leached prior to implantation) thereby to allow pore formation in a medical implant or part thereof.

When the ceramic material acts as a fugitive material, it preferably comprises a controlled release glass which is water soluble.

Said mass of material may include particles having a volume in the range 0.1 to 1 ml, preferably in the range 0.3 to 0.8 ml, more preferably in the range 0.4 to 0.8 ml. Preferably substantially all particles in the mass have a volume as aforesaid.

The average volume (total volume of particles in the mass of material divided by the total number of said particles) may be at least 0.1 ml, preferably at least 0.3 ml, more preferably at least 0.4 ml. The average volume (as described) may be less than 0.8 ml.

Said mass of material may include particles having a diameter of at least 1 mm, preferably at least 2 mm. The diameter may be less than 6 mm, preferably less than 5 mm, more preferably less than 4 mm. Preferably, substantially all particles in the mass have diameters as aforesaid.

The average diameter (sum of diameters of all particles divided by the total number) of said particles may be at least 1 mm, preferably at least 2 mm. The average diameter may be less than 6 mm, preferably less than 5 mm, more preferably less than 4 mm.

Said mass of material may include particles having a weight in the range 0.01 g to 0.1 g, suitably in the range 0.02 g to 0.08 g, preferably in the range 0.03 g to 0.06 g. Preferably, substantially all particles in the mass have an average weight as aforesaid.

The average weight of particles in the mass of material (i.e. total weight of all particles divided by the total number) may be in the range 0.01 g to 0.1 g, suitably in the range 0.02 g to 0.08 g, preferably in the range 0.03 g to 0.06 g. Preferably, substantially all particles in the mass have an average weight as aforesaid.

Said particles are preferably pellets or granules.

Said mass of material may include at least 1 kg, preferably at least 5 kg, of particles.

Said mass of material may include particles comprising 10 to 90 wt %, suitably 20 to 80 wt %, preferably 30 to 80 wt %, more preferably 40 to 80 wt % of ceramic material. The mass of material may, in some cases include 50 to 80 wt %, 60 to 80 wt % or even 70 to 80 wt % of ceramic material.

Said mass of material may include 10 to 90 wt %, suitably 20 to 80 wt %, preferably 30 to 80 wt %, more preferably 40 to 80 wt % of ceramic material. The mass of material may, in some cases include 50 to 80 wt %, 60 to 80 wt % or even 70 to 80 wt % of ceramic material.

Said mass of material preferably consists essentially of said polymeric material and ceramic material.

Said mass of material may include 10 to 90 wt %, preferably 20 to 80 wt %, more preferably 20 to 60 wt %, of said polymeric material. In some cases, the mass of material may include 20 to 50 wt %, 20 to 40 wt % or 20 to 30 wt % of said polymeric material.

The ratio of the weight of polymeric material to the weight of ceramic material in said mass of material may be at least 0.1, preferably at least 0.2. Said ratio may be less than 10, preferably 8 or less, more preferably 5 or less. In some cases, the ratio may be in the range 0.25 to 1.

Where the mass of material includes more than one type of polymeric material which is arranged to define a matrix within which ceramic material is dispersed, weights (or other quantities) of said polymeric material referred to herein may refer to the sum of the total weight of all polymeric materials which are arranged to define a said matrix. Preferably, however, weights (or other quantities) of polymeric materials arranged to define a matrix refer to the weight of a single polymeric material. Preferably, said mass of material for example particles as described, include a single polymeric material which is arranged to define a matrix within which ceramic material is dispersed.

Whereas the mass of material includes more than one ceramic material dispersed within polymeric material, weights (or other quantities) of said ceramic material referred to herein may refer to the sum of the total weight of all ceramic materials. Preferably, however, weights (or other quantities) of ceramic materials refer to the weight of a single ceramic material. Preferably, said mass of material for example particles as described, include a single ceramic material dispersed within polymeric material.

Preferably, at least 90 wt %, more preferably at least 95 wt %, especially about 100% of said mass of material is made up of a single polymeric material and ceramic material.

Said mass of material suitably comprises a homogenous mass, for example of homogenous particles, comprising said polymeric material and ceramic material. Preferably, the ceramic material is dispersed and/or distributed throughout the polymeric material. Preferably, the ceramic material is arranged and distributed so that a large proportion of particles of ceramic material contact other particles of ceramic material—i.e. preferably a negligible number of particles of ceramic material are completely encased in said polymeric material. This may be achieved by using high levels of ceramic material and ensuring that polymeric material and ceramic material are fully mixed to produce a homogenous mass.

Preferably, said mass of material, for example particles, includes fused polymeric material, for example fused particles of polymeric material. Said fused polymeric material suitably defines a network which is suitably substantially continuous throughout said mass of material, for example through a said particle thereof. Said network is suitably irregularly shaped. Ceramic material in said mass, for example in a particle may be arranged between parts of and/or may contact said network. Ceramic material may comprise discrete particles which may contact one another but are preferably not fused to one another. Preferably, at least 80%, more preferably at least 90 wt %, especially substantially all particles in said mass of material are as described.

Said mass of material, for example particles, are preferably obtainable in a process which comprises melt processing, for example, extruding, polymeric material and ceramic material.

An extrudate, for example in the form of a lace, may be cut for example chopped, to define particles.

Said polymeric material may have a Notched Izod Impact Strength (specimen 80 mm×10 mm×4 mm with a cut 0.25 mm notch (Type A), tested at 23° C., in accordance with ISO180) of at least 4 $KJm^{-2}$, preferably at least 5 $KJm^{-2}$, more preferably at least 6 $KJm^{-2}$. Said Notched Izod Impact Strength, measured as aforesaid, may be less than 10 $KJm^{-2}$, suitably less than 8 $KJm^{-2}$.

The Notched Izod Impact Strength, measured as aforesaid, may be at least 3 $KJm^{-2}$, suitably at least 4 $KJm^{-2}$, preferably at least 5 $KJm^{-2}$. Said impact strength may be less than 50 $KJm^{-2}$, suitably less than 30 $KJm^{-2}$.

Said polymeric material suitably has a melt viscosity (MV) of at least 0.06 $kNsm^{-2}$, preferably has a MV of at least 0.09 $kNsm^{-2}$, more preferably at least 0.12 $kNsm^{-2}$, especially at least 0.15 $kNsm^{-2}$.

MV is suitably measured using capillary rheometry operating at 400° C. at a shear rate of 1000 $s^{-1}$ using a tungsten carbide die, 0.5×3.175 mm.

Said polymeric material may have a MV of less than 1.00 $kNsm^{-2}$, preferably less than 0.5 $kNsm^{-2}$.

Said polymeric material may have a MV in the range 0.09 to 0.5 $kNsm^{-2}$, preferably in the range 0.14 to 0.5 $kNsm^{-2}$, more preferably in the range 0.3 to 0.5 $kNsm^{-2}$.

Said polymeric material may have a tensile strength, measured in accordance with ISO527 (specimen type 1b) tested at 23° C. at a rate of 50 mm/minute of at least 20 MPa, preferably at least 60 MPa, more preferably at least 80 MPa. The tensile strength is preferably in the range 80-110 MPa, more preferably in the range 80-100 MPa.

Said polymeric material may have a flexural strength, measured in accordance with ISO178 (80 mm×10 mm×4 mm specimen, tested in three-point-bend at 23° C. at a rate of 2 mm/minute) of at least 50 MPa, preferably at least 100 MPa, more preferably at least 145 MPa. The flexural strength is preferably in the range 145-180 MPa, more preferably in the range 145-164 MPa.

Said polymeric material may have a flexural modulus, measured in accordance with ISO178 (80 mm×10 mm×4 mm specimen, tested in three-point-bend at 23° C. at a rate of 2 mm/minute) of at least 1 GPa, suitably at least 2 GPa, preferably at least 3 GPa, more preferably at least 3.5 GPa. The flexural modulus is preferably in the range 3.5-4.5 GPa, more preferably in the range 3.5-4.1 GPa.

Said polymeric material may be amorphous or semi-crystalline. It is preferably semi-crystalline.

The level and extent of crystallinity in a polymer is preferably measured by wide angle X-ray diffraction (also referred to as Wide Angle X-ray Scattering or WAXS), for example as described by Blundell and Osborn (Polymer 24, 953, 1983). Alternatively, crystallinity may be assessed by Differential Scanning calorimetry (DSC).

The level of crystallinity of said polymeric material may be at least 1%, suitably at least 3%, preferably at least 5% and more preferably at least 10%. In especially preferred embodiments, the crystallinity may be greater than 25%.

The main peak of the melting endotherm (Tm) of said polymeric material (if crystalline) may be at least 300° C.

Said polymeric material may include a repeat unit of general formula

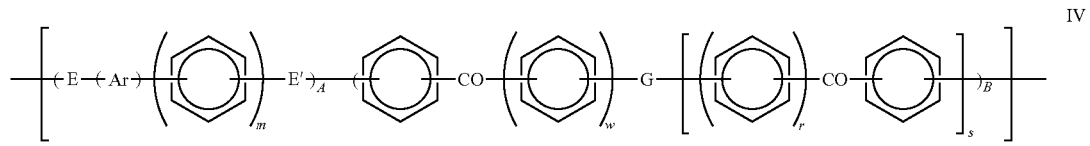

IV or a repeat unit of general formula

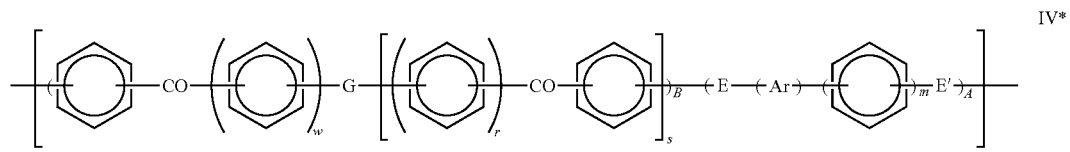

IV* wherein A and B independently represent 0 or 1, E and E' independently represent an oxygen or a sulphur atom or a direct link, G represents an oxygen or sulphur atom, a direct link or a —O-Ph-O— moiety where Ph represents a phenyl group, m, r, s, t, v, w, and z represent zero or 1 and Ar is selected from one of the following moieties (i) to (v) which is bonded via one or more of its phenyl moieties to adjacent moieties

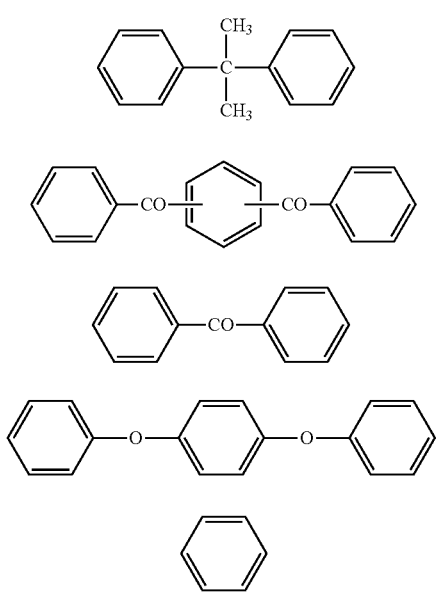

(i)
(ii)
(iii)
(iv)
(v)

Unless otherwise stated in this specification, a phenyl moiety has 1,4-, linkages to moieties to which it is bonded.

Said polymeric material may be a homopolymer which includes a repeat unit of IV or IV*.

Preferably, said polymeric material is a homopolymer having a repeat unit of general formula IV.

Preferably Ar is selected from the following moieties (vi) to (x)

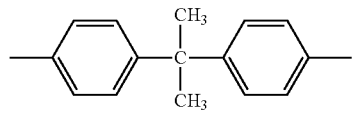

(vi)

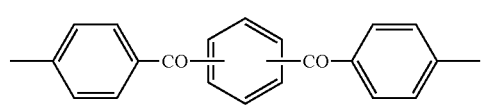

(vii)

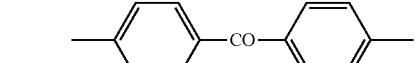

(viii)

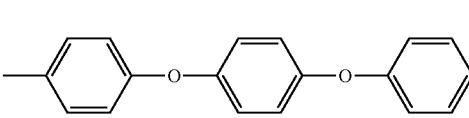

(ix)

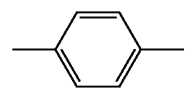

(x)

In (vii), the middle phenyl may be 1,4- or 1,3-substituted. It is preferably 1,4-substituted.

Suitable moieties Ar are moieties (ii), (iii), (iv) and (v) and, of these, moieties, (ii), (iii) and (v) are preferred. Other preferred moieties Ar are moieties (vii), (viii), (ix) and (x) and, of these, moieties (vii), (viii) and (x) are especially preferred.

An especially preferred class of polymeric materials are polymers (or copolymers) which consist essentially of phenyl moieties in conjunction with ketone and/or ether moieties. That is, in the preferred class, the polymer material does not include repeat units which include —S—, —SO$_2$— or aromatic groups other than phenyl. Preferred bio-compatible polymeric materials of the type described include:

(a) a polymer consisting essentially of units of formula IV wherein Ar represents moiety (v), E and E' represent oxygen atoms, m represents 0, w represents 1, G represents a direct link, s represents 0, and A and B represent 1 (i.e. polyetheretherketone).

(b) a polymer consisting essentially of units of formula IV wherein E represents an oxygen atom, E' represents a direct link, Ar represents a moiety of structure (ii), m represents 0, A represents 1, B represents 0 (i.e. polyetherketone);

(c) a polymer consisting essentially of units of formula IV wherein E represents an oxygen atom, Ar represents moiety (ii), m represents 0, E' represents a direct link, A represents 1, B represents 0, (i.e. polyetherketoneketone).
(d) a polymer consisting essentially of units of formula IV wherein Ar represents moiety (ii), E and E' represent oxygen atoms, G represents a direct link, m represents 0, w represents 1, r represents 0, s represents 1 and A and B represent 1. (i.e. polyetherketoneetherketoneketone).
(e) a polymer consisting essentially of units of formula IV, wherein Ar represents moiety (v), E and E' represents oxygen atoms, G represents a direct link, m represents 0, w represents 0, s, r, A and B represent 1 (i.e. polyetheretherketoneketone).
(f) a polymer comprising units of formula IV, wherein Ar represents moiety (v), E and E' represent oxygen atoms, m represents 1, w represents 1, A represents 1, B represents 1, r and s represent 0 and G represents a direct link (i.e. polyether-diphenyl-ether-phenyl-ketone-phenyl-).

Said polymeric material may consist essentially of one of units (a) to (f) defined above. Alternatively, said polymeric material may comprise a copolymer comprising at least two units selected from (a) to (f) defined above. Preferred copolymers include units (a). For example, a copolymer may comprise units (a) and (f); or may comprise units (a) and (e).

Said polymeric material preferably comprises, more preferably consists essentially of, a repeat unit of formula (XX)

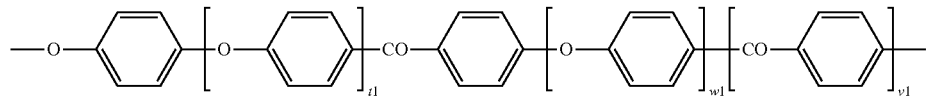

where t1, and w1 independently represent 0 or 1 and v1 represents 0, 1 or 2. Preferred polymeric materials have a said repeat unit wherein t1=1, v1=0 and w1=0; t1=0, v1=0 and w1=0; t1=0, w1=1, v1=2; or t1=0, v1=1 and w1=0. More preferred have t1=1, v1=0 and w1=0; or t1=0, v1=0 and w1=0. The most preferred has t1=1, v1=0 and w1=0.

In preferred embodiments, said polymeric material is selected from polyetheretherketone, polyetherketone, polyetherketoneetherketoneketone and polyetherketoneketone. In a more preferred embodiment, said polymeric material is selected from polyetherketone and polyetheretherketone. In an especially preferred embodiment, said polymeric material is polyetheretherketone.

Said ceramic material suitably has a melting point which is greater than the melting point of said polymeric material. The melting point of the ceramic material may be at least 100° C., suitably at least 200° C., preferably at least 300° C., more preferably at least 350° C. greater than the melting point of said polymeric material. The melting point of the ceramic material may be at least 450° C., preferably at least 500° C., more preferably at least 600° C., especially at least 700° C.

Said ceramic material preferably has a glass transition temperature which is greater than the melting point of said polymeric material, for example by at least 10° C., or at least 50° C. or at least 100° C.

Said mass of material may include discrete particles of ceramic material which are suitably dispersed in the polymeric material. Said ceramic material dispersed in particles in said mass of material may have a $D_{50}$ in the range 1 to 20000 µm. Preferably, the $D_{50}$ is in the range 10 to 2000 µm. In some embodiments wherein, for example, the mass of material is to be used to produce a porous member to be used in an osseoconductive capacity, the $D_{50}$ may be in the range 10 to 1200 µm to allow pores to be produced which are suitable for bone ingrowth. In other embodiments, lower porosity may be required in which case the $D_{50}$ may be in the range 10 to 100 µm.

In some embodiments, said ceramic material or part of said ceramic material may be arranged to be leached from a part in which it is incorporated, for example an implant when the implant is in situ in a human body. Said mass of material may include a further active material which may be arranged to have a beneficial effect when liberated. For example, said active material which may be dissolved from a part, for example an implant, made from a said mass of material may comprise an active material, for example an anti-bacterial agent (e.g. silver or anti-biotic containing), a radioactive compound (e.g. which emits alpha, beta or gamma radiation for therapy, research, tracing, imaging, synovectomy or microdosimetry) or an active agent which may facilitate bone integration or other processes associated with bone (e.g. the active agent may be calcium phosphate).

Said mass of material may include other additives, for example, reinforcing agents which may comprise additives which are arranged to improve mechanical properties of components made from the mass of material. Preferred reinforcing agents comprise fibres.

Said fibres may comprise a fibrous filler or a non-fibrous filler. Said fibres may include both a fibrous filler and a non-fibrous filler.

A said fibrous filler may be continuous or discontinuous. In preferred embodiments a said fibrous filler is discontinuous.

Preferably, fibres which are discontinuous have an average length of less than 10 mm, preferably less than 7 mm.

A said fibrous filler may be selected from inorganic fibrous materials, high-melting organic fibrous materials and carbon fibre.

A said fibrous filler may be selected from inorganic fibrous materials, non-melting and high-melting organic fibrous materials, such as aramid fibres, and carbon fibre.

A said fibrous filler may be selected from glass fiber, carbon fibre, asbestos fiber, silica fiber, alumina fiber, zirconia fiber, boron nitride fiber, silicon nitride fiber, boron fiber, fluorocarbon resin fibre and potassium titanate fiber. Preferred fibrous fillers are glass fibre and carbon fibre.

A fibrous filler may comprise nanofibres.

A said non-fibrous filler may be selected from mica, silica, talc, alumina, kaolin, calcium sulfate, calcium carbonate, titanium oxide, ferrite, clay, glass powder, zinc oxide, nickel carbonate, iron oxide, quartz powder, magnesium carbonate, fluorocarbon resin and barium sulfate. The list of non-fibrous fillers may further include graphite, carbon powder and nanotubes. The non-fibrous fillers may be introduced in the form of powder or flaky particles.

Preferred reinforcing agents are glass fibre and/or carbon fibre.

Other additives may comprise radiopacifiers, for example barium sulphate and any other radiopacifiers described in co-pending application PCT/GB2006/003947. Up to 20 wt %, or up to 5 wt % of radiopacifiers may be included. Preferably, less than 1 wt %, more preferably no radiopacifier is included.

Other additives may include colourants, for example titanium dioxide. Up to 3 wt % of colourant may be included but preferably less than 1 wt %, more preferably no, colourant is included.

Said mass of material may include up to 15 wt %, for example up to 10 wt % of other materials—that is, in addition to said polymeric material and ceramic material. Thus in one preferred embodiment, said mass of material includes 20 to 80 wt % of ceramic material (preferably of a single type of ceramic material), 20 to 80 wt % of a polymeric material (preferably of a single type of polymeric material) and up to 15 wt % of other materials, for example of the type described. In another preferred embodiment, said mass of material includes 40 to 80 wt % of ceramic material (preferably of a single type of ceramic material), 20 to 60 wt % of a polymeric material (preferably of a single type of polymeric material) and up to 10 wt % of other materials, for example of the type described. In a further preferred embodiment, said mass of material includes 55 to 80 wt % of ceramic material (preferably of a single type of ceramic material), 20 to 45 wt % of a polymeric material (preferably of a single type of polymeric material) and up to 5 wt % of other materials, for example of the type described.

Preferably, said mass of material, for example particles, consists essentially of polymeric material and ceramic material and more preferably consists essentially of a single type of polymeric material and a single type of ceramic material.

According to a second aspect of the invention, there is provided a method of making a mass of material according to the first aspect, the method comprising:
(a) contacting a polymeric material and a ceramic material as described according to the first aspect; and
(b) forming said mixture into a mass of material.

The mass of material, particles, polymeric material and ceramic material may have any feature described in said first aspect.

At the end of step (a), the mixture is preferably substantially homogenous. In step (a), initial contact may occur at ambient temperature; for example polymeric material and ceramic material may be dry mixed. Alternatively and preferably, ceramic material may be initially contacted with polymeric material at above ambient temperature for example when the polymeric material is molten. In a preferred embodiment, ceramic material is initially contacted with polymeric material in a compounder for example in the screw of a compounder.

Preferably, said polymeric material and ceramic material are melt-processed. This may involve moulding (e.g. compression or injection) or extrusion or the like.

When said mass of material includes other additives as described according to said first aspect, said other additives may be included in a mixture which is melt processed. It is preferred that additives are selected which can withstand the processing conditions used in the method of the second aspect.

Melt-processing of the mixture may be undertaken in an extruder. Thus, polymeric material and ceramic material may be mixed and/or melt processed in an extruder. The polymeric material and ceramic material may be melt processed to define particles by extruding a length of mixture and comminuting said length, for example by cutting, chopping or the like, to define particles of the type described. Such particles suitably comprise fused polymeric material which is suitably defined by polymeric material melted in the melt-processing such that said polymeric material suitably defines a network; and ceramic material arranged within the network, wherein said ceramic material is not melted by said melt-processing.

The mixture is suitably melt-processed to define said particles described which are suitably then cooled.

According to a third aspect of the invention, there is provided a method of making a component, the method comprising:
(a) melt-processing a polymeric material and a ceramic material, each being as described according to the first aspect, to define at least a part of the component;
(b) optionally, removing the ceramic material.

Said polymeric material and ceramic material may be included in a mass of material as described according to the first aspect and/or such a mass of material may be made in a method according to the second aspect.

The method may be used in non-medical or medical applications. Non-medical applications include manufacture of filters, meshes, light-weight parts and parts arranged to elute active materials, for example lubricants.

The component may comprise a part or the whole of a device which may be incorporated into or associated with a human body. Thus, the component may suitably be a part of or the whole of a medical implant. The medical implant may be arranged to replace or supplement soft or hard tissue. It may replace or supplement bone. It may be used in addressing trauma injury or craniomaxillofacial injury. It may be used in joint replacement, for example as part of a hip or finger joint replacement; or in spinal surgery.

In the method, said mass of material is suitably melt processed at a temperature above the melting temperature of polymeric material in said mass of material but at a temperature which is less than the melting temperature of the ceramic material.

Said mass of material may be melt-processed in any known manner. It is preferably melt processed in an extruder or moulder, for example injection moulder. Extrusion or moulding may be used to directly produce said component (or part thereof); or may be used to produce a precursor of said component (or part thereof) which may be subjected to further processing, for example machining, to define said component (or part thereof).

When said mass of material is melt processed in an extruder, a fibre, rod, tube, bar, plate or film may be produced. A rod, tube, bar or plate may define a precursor of a said component (or part thereof) which may be further processed for example by machining. A said film may itself be used directly or may be associated with other materials to define a device. References to extrusion include co-extrusion to define components which include regions of different compositions and/or properties.

A said component may include a hollow or void region.

When said mass of material is melt processed in a moulder any desired shape may be produced. Near net-shaped ingots may be produced for further processing, for example machining; or a component which does not require any significant machining prior to use may be produced. An injection moulder is a preferred moulder. References to moulding include overmoulding to define components which include regions of different compositions and/or properties.

A particularly advantageous method may comprise making a component (or part thereof) which includes regions of different compositions. For example, a first region may be made by moulding a said mass of material of the type described; and a second region may be made by moulding a second region adjacent the first region, wherein said second region is moulded from a second composition which is different to the composition of said mass of material. Said second composition may be in the form of a mass of material as described according to the first aspect (e.g. it includes polymeric material and ceramic material) or may not be a mass of material in accordance with the first aspect (e.g. it may not include a ceramic material). In a preferred embodiment, said first and second regions may comprise the same polymeric material, for example polyetheretheketone. The regions may differ on the basis of the amount or identity of ceramic (or other) material used in the preparation of said regions. The component (or part thereof) may include one or a plurality of further regions.

In another method, a component (or part thereof) may be made which includes regions of different porosities or regions which include different levels of ceramic material (and may later define regions of different porosities). For example, a first region may be made by moulding a said mass of material of the type described which includes a first amount of ceramic material; and a second region may be made by moulding a said mass of material of the type described which includes a second amount of ceramic material, wherein said first and second amounts are different. The component may include one or a plurality of further regions. Thus, the method may be used to produce a component (or part thereof) which includes different levels of ceramic material (or porosity if the ceramic material is removed). For example, a component (or part thereof) may include gradually increasing or stepped levels of ceramic material (or porosity) on moving from one position to another position.

In a first embodiment, a component (or part thereof) made in the method may be used, for example as a part or the whole of a device which may be incorporated into or associated with a human body, only after ceramic material has been removed in step (b) of the method. In this case, the method may be used to define a component (or part thereof) which is porous prior to use. The ceramic materials sole purpose in the method may be to facilitate such pore formation.

In a second embodiment, a component (or part thereof) made in the method may be arranged to be used, for example as a part or the whole of a device which may be incorporated into or associated with a human body, whilst ceramic material remains associated with the device and/or prior to any removal of ceramic material. Thus, the ceramic material is suitably of a type which has no detrimental effects when present in a human body. Preferably, such a ceramic material is arranged to leach out of the component (or part thereof) in vivo. Suitably, leaching of said ceramic material is arranged to produce increasing levels of porosity in said component (or part thereof) in vivo. Such porosity may also be arranged to have a positive effect.

The method of the third aspect may be used in overmoulding a substrate (e.g. a moulded part) with a mixture comprising polymeric material and ceramic material or may be used in coating a substrate with a mixture comprising polymeric material and ceramic material. After overmoulding or coating, the ceramic material may optionally be leached or it may leach in use, optionally to deliver an active material which may be included in the mixture used for overmoulding or coating.

In a third embodiment, a component (or part thereof) made in the method may be treated to remove its ceramic material as described in accordance with the first embodiment. Thereafter, porous regions of the component (or part thereof) may be impregnated with another material. Such a material may be arranged to leach from the component (or part thereof) in vivo or may be arranged to remain within pores in the component (or part thereof) and exert an effect, for example a biological effect, when present. An example of a material which may be impregnated as aforesaid is collagen or a drug loaded bioabsorbable polymer.

In a fourth embodiment, a component (or part thereof) of the first, second or third embodiments may include a hollow or void region which may be impregnated with another material as described in the third embodiment.

When said method includes removing said ceramic material in step (b), the method suitably involves contacting a product formed after melt-processing in step (a) with a means for removing the ceramic material, suitably so as to define porosity. Contact may take place at any time. However, contact suitably takes place after any machining or physical manipulation of said product that may be involved in making a component (or part thereof) for use, for example as part of or the whole of a device which may be incorporated into or associated with a human body. This is because a product may have more strength to withstand, for example machining, whilst ceramic material is in situ.

Said means for removing the ceramic material may be arranged to solubilise said ceramic material. Said means suitably comprises a solvent. Said solvent may be non-aqueous or aqueous. Said solvent preferably comprises water and more preferably includes at least 80 wt %, preferably at least 95 wt %, especially at least 99 wt % water. The solvent preferably consists essentially of water.

Means for removing the ceramic material may comprise contacting the product formed after melt processing with a solvent formulation (preferably comprising water as aforesaid) which is at a temperature of greater than 100° C. and a pressure above ambient pressure thereby to charge the solvent formulation with ceramic material and separating the charged solvent from the product.

In the method, said solvent formulation may be at a temperature of greater than 150° C., suitably greater than 200° C. when contacted with said product. Said solvent formulation may be at a temperature of less than 500° C., suitably less than 450° C., preferably less than 400° C., more preferably less than 350° C. when contacted with said product.

The solvent formulation may be under a pressure of at least 4 bar, suitably at least 8 bar, preferably at least 10 bar when contacted with said product. The pressure may be less than 300 bar, preferably less than 200 bar, more preferably less than 100 bar, especially less than 50 bar. The pressure is preferably selected to maintain the solvent formulation in the liquid state when in contact with said product.

Preferably, in the method, the solvent formulation is arranged to flow from a first region to a third region via a second region in which said product is arranged.

According to a fourth aspect, there is provided a component or part thereof obtainable in the method of the third aspect.

According to a fifth aspect, there is provided a medical implant for implantation in a human body, said medical implant comprising a material which includes polymeric material and a ceramic material, wherein said polymeric material is of a type which includes:

(a) phenyl moieties;
(b) ketone moieties; and
(c) ether moieties;

wherein the ceramic material is a bioactive glass and/or a controlled release glass, wherein said ceramic material includes less than 20 mole % sodium oxide and/or is water soluble.

The material of the fifth aspect may have any feature of the mass of material of the first aspect.

Said medical implant may be arranged to replace or supplement soft or hard tissue. It may replace or supplement bone.

Preferably, the porosity of said medical implant is arranged to increase after implantation in a human body for example by dissolution of the ceramic material.

Any feature of any aspect of any invention or embodiment described herein may be combined with any feature of any aspect of any invention or embodiment described herein mutatis mutandis.

Specific embodiments of the invention will now be described, by way of example, with reference to the accompanying drawings, in which:

FIGS. 1a and 1b are a perspective view and a cross-section respectively of an acetabular cup with an overmoulded porous layer; and FIGS. 2a and 2b are a perspective view and a cross-section respectively of an alternative acetabular cup with an overmoulded area of porous material of one type and an adjacent overmoulded area of another material; and FIG. 3 is a schematic representation of an implantable device comprising areas having different properties.

As an initial step, attempts were made to melt process polyetheretherketone (PEEK) and selected glasses using the general procedure described in Example 1 and the specific glasses described in Examples 2 to 5. The glasses selected were as follows:

Bioactive glass 45S5—a common and widely commercially available bioactive glass comprising $SiO_2$ (46 mol %), $Na_2O$ (24 mol %), $CaO$ (27 mol %), $P_2O_5$ (3 mol %).

Bioactive glass 13-93 glass powder—a bioactive glass comprising $SiO_2$ (53 wt %), $Na_2O$ (6 wt %), $K_2O$ (12 wt %), $CaO$ (20 wt %), $P_2O_5$ (4 wt %), $MgO$ (5 wt %).

Bioactive glass 13-92—glass powder having 0 wt % $Na_2O$.

Controlled release glass—Obtained from Mo-Sci and having nominal composition—$Ag_2O$ (1-30 wt %), $Li_2O$, $Na_2O$, $K_2O$ (0-12 wt %), $Al_2O_3$ (0-5 wt %), $P_2O_5$ (0-70 wt %) and $B_2O_3$ (40-80 wt %) (referred to herein as CRG-1).

Example 1

General Procedure for Melt Processing

Prior to attempted compounding, the raw materials—unfilled polyetheretherketone (PEEK) polymer with medium viscosity (Invibio LT2 obtained from Invibio Limited, UK) and a selected glass were prepared. To aid removal of atmospheric water and benefit processing, the selected glass was placed in a drying oven for 5 hours at 200° C. This was repeated for the PEEK to remove the 0.5% of water which PEEK absorbs.

A twin-screw compounder was used, fitted with a strand die and suitable polymer and powder metering equipment. The selected glass and PEEK raw materials were hand charged to two compounder hoppers. At the output end a strand conveyer, a pelletiser, a classifier to separate longs and a suitable clean collection bin were positioned. An appropriate size of machine was chosen to reduce excessive polymer residence time. The addition of the glass to the PEEK polymer occurred via a side feeder on the extruder, when the polymer was in a fluid state (due to shear and temperature generated in the screw). A lower viscosity PEEK polymer (medium viscosity LT2) was selected to help counteract the increase in viscosity as a result of the addition of high quantities of filler. The twin-screw compounder ran at a temperature between 360-400° C. A normal screw profile fabricated from stainless steel was used with a minimum L/D ratio of 45:1. At the extrusion end a twin hole die with a 4 mm orifice was used. The temperature profile along the screw varied between 360-400° C.

The main screw rotation speed was set at 150-250 rpm (but could be higher for highly loaded materials). It was maintained within the former range to avoid long residence times and potential polymer degradation.

Examples 2 to 5

Compounding PEEK and Selected Glasses

Following the procedure of Example 1, attempts were made to compound various glasses. Details and results are provided in Table 1.

TABLE 1

| Example No | Amount of PEEK (wt %) | Identity of glass | Amount of glass (wt %) | Result |
|---|---|---|---|---|
| 2 | 50 | 45S5 | 50 | Reaction when materials contacted occurred rapidly producing a very high viscosity mixture which prevented any further flow. |
| 3 | 50 | 13-93 | 50 | High viscosity mixture not produced (unlike example 2) |
| 4 | 50 | 13-92 | 50 | High viscosity mixture not produced (unlike example 2) |
| 5 | 50 | Controlled Release Glass CRG-1 | 50 | High viscosity mixture not produced (unlike example 2) |

It will be appreciated that the 455S glass cannot be melt processed due to the very high viscosity resulting on melting which shows that PEEK and the glass are not compatible. Investigations undertaken suggest the polymeric is unstable, presumably due to reaction with the glass. The other glasses may be melt processible to produce useful products, particularly if the number of melt processing cycles to which the PEEK/glass mixture is subjected is minimised. The Example 5 material, however, can readily be melt processed through numerous cycles.

Compatible PEEK/glass combinations may be used to prepare granules using the general process of Example 7 and, in turn, the granules may be used to produce desired shapes using the general processes of Examples 8 to 13.

Example 7

Preparing Granules

Prior to compounding, the raw materials—unfilled (polyetheretherketone) PEEK polymer with medium viscosity (Invibio LT2 obtained from Invibio Limited, UK) and a selected glass were prepared. The glass may be sorted to an appropriate particle size suited to give pores for osseoconductivity (particle range 100-1000 µm diameter), if required. This may be achieved through sieving through graduated meshes. To aid the removal of atmospheric water and benefit processing, the PEEK and glass may be dried in an oven prior to use.

A twin-screw compounder fitted with a strand die and suitable polymer and powder metering equipment may be used. The glass and PEEK raw materials may be charged to two compounder hoppers. At the output end a strand conveyer, a pelletiser, a classifier to separate longs and a suitable clean collection bin may be provided. An appropriate size of machine may be chosen to reduce excessive residence time. The glass and PEEK may be fed in at a suitable ratio, with the addition of the glass occurring when the polymer is in a fluid state (due to shear and temperature generated in the screw). A lower viscosity PEEK polymer may be selected to help counteract the increase in viscosity as a result of the addition of high quantities of filler. The twin-screw compounder may be run at a temperature between 360-400° C. At the extrusion end a twin hole die with a 4 mm orifice may be used.

The main screw rotation speed may be 150-250 rpm (but could be higher for highly loaded materials). It may be maintained within the former range to avoid long residence times. The compounded material may be extruded as a continual lace of approximately 3 mm. This may be air cooled as it is captured onto a strand conveyer. To convert laces to pellets, a pelletiser may be used.

Example 8

Injection Moulding of Granules into Near Net Shape Ingots

Ingots of dimensions 20 mm×20 mm×100 mm, suitably for machining, may be made in an injection moulding machine using granules of Example 1.

Example 9

Injection Moulding of Granules into Plaques

The procedure described in Example 8 may be followed to prepare 150 mm×75 mm×10 mm plaques which may be machined into representative samples for medical devices which may benefit from porosity.

Example 10

Formation of Partially Porous Regions

Near net shaped ingots of dimensions 20 mm×20 mm×100 mm having partially porous regions may be made. Within a mould tool cavity preformed ingots may be placed, these being manufactured using the technique described in Example 8, but subsequently machined to remove a predetermined volume to produce half ingots and other partial ingots. The half and partial ingots may be solid ingots that have been machined to remove sufficient volume to permit the flow of new polymer into the remaining mould cavity space when the ingots are re-inserted into the mould tool. Unfilled PEEK (or an alternative mixture comprising polymer plus optional filler) may be charged into the injection moulding machine reading for injection into the remaining cavity space.

Example 11

Extrusion into Rod Stock

Rod stock may be made using granules by extrusion. The rod stock could be machined to define a medical device and subsequently porosity produced in vivo by removal of the glass.

Example 12

Formation of Film

To create film and thin sheets of material from granules of Example 7, a template consisting of several parts sandwiched together may be used. To the underside of a metal plate with a central shape cut-out (typically a square) and of 1 mm thickness may be placed a thin aluminium foil sheet, coated with non-stick agent to facilitate release. Into the central cut-out sufficient granules may be placed to cover roughly the cut-out area and to overfill the tool to allow for shrinkage.

Example 13

Large Scale Film Production

Film may be prepared by extruding granules through a slit die to define film of desired dimensions.

Example 14

Injection Moulding into Direct Device or Component Shape

By following the methods described above, granules of Example 7 may be fed to an injection moulding machine with mould cavities arranged to define a part or the whole of a medical device without machining.

The processes and/or products described in the aforementioned examples may have wide scale applications.

In general terms the granules may be used in any situation where standard granules comprising filled or unfilled polyetheretherketone may be used. These include extrusion, co-extrusion, moulding or overmoulding processes.

Films may be prepared to replace soft or hard tissues. Such an arrangement may be of utility in treatment of trauma or craniomaxillofacial injury where a thin supporting layer may be required for structural reinforcement. The provision of pores in the material (which may form by leaching of the glass in vivo) facilitates tissue anchorage and integration through in-growth.

Tubing may be made using granules comprising a glass at a suitable loading and of appropriate particle sizes, by melting the granules and extruding material through a dye to form a tube shape. This shape can be cooled (eg. in air on a conveyor line) and cut into lengths. The tubes can be made rigid or thin walled depending on the proposed application and may have applications as components, or as functional parts. The lumen of the tube could remain empty, be filled with unfilled, or filled PEEK, or another polymer, or metal. This additional material in the lumen can be inserted and permanently bonded using melt processes (eg. over extrusion onto a material). The internal material may contain factors that pass out through pores formed by dissolution of the glass to convey a particular activity within a structural porous PEEK tube of pore sizes in the range 1 to 1000 μm depending on application.

By way of example, small diameter tubing/hollow fibres possessing microporosity may be made for use as a bone ingrowth fibre using a glass. The glass could resorb in-vivo to leave pores for cell ingrowth.

In another embodiment, screws or bolts used in medical applications in vivo may be overmoulded using the granules described to allow insertion but, by defining specific porous formed by dissolution of the glass, tissue ingrowth may be improved.

Mono or multi-filament fibres may be made by extrusion using the granules. Porosity may be formed in vivo. Fibres may be used for sutures or yarns that could be subsequently woven or braided or knitted or non-woven into textiles suitable for implantation.

Granules may be used in the manufacture of devices requiring better fixation or tissue integration. Referring to FIG. 6, a polymeric acetabular cup includes a cup body 2 which may be made from a composite material comprising PEEK and carbon fibre and an overmoulded outer layer 4 comprising a polymer, for example PEEK containing a glass which may be overmoulded from granules made as described in Example 7. The glass may leach from layer 4 in vivo leaving a porous layer 4 which may facilitate tissue integration.

In a further variation illustrated in FIGS. 7a and 7b, an acetabular cup includes cup body 2 and an outer layer 4 which this time only covers a hemispherical surface. The other hemispherical surface 6 may be formed of a different material (e.g. PEEK with an alternative filler or mouldable material such as an elastomer).

In general terms, granules as described may be used in conjunction with other materials to provide combination materials with targeted functional areas to allow devices to be made which may confer beneficial properties in particular regions. For example, referring to FIG. 8, regions 10 may comprise an unfilled or carbon fibre filled PEEK frame arranged to provide the main structural support, closely mimicking bone. Certain areas, for example in regions 12, 14 which may be at an end or on one particular side/area and which may come into contact with bone and require ingrowth, may be moulded to define a potentially porous PEEK and/or comprise PEEK filled with a glass which could resorb during implantation to leave pores.

The invention claimed is:

1. A mass of material comprising a polymeric material and a ceramic material, wherein said polymeric material is of a type which includes:
    (a) phenyl moieties;
    (b) ketone moieties; and
    (c) ether moieties;
wherein the ceramic material is a bioactive glass and/or a controlled release glass, wherein said ceramic material includes less than 20 mole % sodium oxide and/or is water soluble, wherein said mass comprises particles which include said polymeric materials and said ceramic material, wherein said particles have a volume in the range 0.1 to 1 mL and an average weight of particles in the mass of materials is in the range 0.01 g to 0.1 g.

2. A mass according to claim 1, wherein the total amount of sodium oxide in said ceramic material is less than 10 mole % and the total amount of alkali metal oxide in said ceramic material is less than 10 mole %.

3. A mass according to claim 1, wherein said ceramic material comprises a bioactive glass having a network connectivity of 2 or greater and less than 3.2.

4. A mass according to claim 1, wherein said ceramic material comprises a controlled release glass which includes less than 20 mole % silicone dioxide, includes phosphorous pentoxide as a glass former and includes less than 10 mole % of sodium oxide, wherein the total amount of alkali metal oxide in said controlled release glass is less than 10 mole % and wherein said controlled release glass includes an alkaline earth metal oxide or carbonate or oxide or carbonate of a lanthanide.

5. A mass according to claim 1, wherein said bioactive glass includes at least 30 mole % phosphorous pentoxide as a glass former.

6. A mass according to claim 1, wherein said controlled release glass is completely soluble in water at 38° C.

7. A mass according to claim 1, wherein, on dissolution, said controlled release glass has a pH of less than 7.

8. A mass according to claim 1, wherein said mass includes particles comprising 40 to 80 wt % of ceramic material and 20 to 60 wt % of said polymeric material.

9. A mass according to claim 1, wherein said mass includes 60 to 80 wt % of ceramic material and 20 to 40 wt % of polymeric material.

10. A mass according to claim 1, wherein said polymeric material comprises a repeat unit of formula (XX)

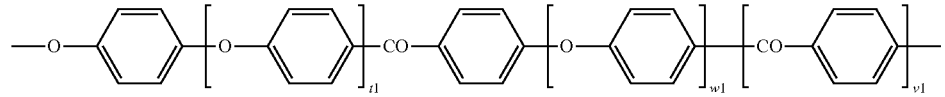

where t1 and w1 independently represent 0 or 1 and v1 represents 0, 1 or 2.

11. A mass according to claim 1, wherein said polymeric material is selected from polyetheretherketone, polyetherketone, polyetherketoneetherketoneketone and polyetherketoneketone.

12. A mass according to claim 1, wherein said polymeric material is polyetheretherketone.

13. A mass according to claim 1, wherein said mass consists essentially of a single type of polymeric material and a single type of ceramic material.

14. A mass according to claim 1, wherein said mass of material comprises homogeneous particles comprising said polymeric material and ceramic material and said particles include a fused polymeric material.

15. A mass of material comprising a polymeric material and a ceramic material, wherein said polymeric material is of a type which includes:
    (a) phenyl moieties;
    (b) ketone moieties; and
    (c) ether moieties,
    wherein the ceramic material is a bioactive glass and/or a controlled release glass, wherein said ceramic material includes less than 10 mole % sodium oxide and/or is water soluble and wherein the total amount of alkali metal oxide in said ceramic material is less than 10 mole %.

16. The mass according to claim 15, wherein said polymeric material is polyetheretherketone and said mass of material comprises homogenous particles comprising said polymeric material and ceramic material and said particles include a fused polymeric material.

17. A mass of material comprising a polymeric material and a ceramic material, wherein said polymeric material is of a type which includes:
 (a) phenyl moieties;
 (b) ketone moieties; and
 (c) ether moieties,
 wherein said ceramic material comprises a controlled release glass which includes less than 20 mole % silicone dioxide, includes phosphorous pentoxide as a glass former, and includes less than 10 mole % of sodium oxide, wherein the total amount of alkali metal oxide in said controlled release glass is less than 10 mole % and wherein said controlled release glass includes an alkaline earth metal oxide or carbonate or oxide or carbonate of a lanthanide.

18. The mass according to claim 17, wherein said polymeric material is polyetheretherketone and said mass of material comprises homogenous particles comprising said polymeric material and ceramic material and said particles include a fused polymeric material.

19. A mass of material comprising a polymeric material and a ceramic material, wherein said polymeric material is of a type which includes:
 (a) phenyl moieties;
 (b) ketone moieties; and
 (c) ether moieties,
 wherein the ceramic material is a bioactive glass, wherein said ceramic material includes less than 20 mole % sodium oxide and/or is water soluble, wherein said bioactive glass includes at least 30 mole % phosphorous pentoxide as a glass former.

20. The mass according to claim 19, wherein said polymeric material is polyetheretherketone and said mass of material comprises homogenous particles comprising said polymeric material and ceramic material and said particles include a fused polymeric material.

* * * * *